US009050050B2

(12) United States Patent
Carney et al.

(10) Patent No.: US 9,050,050 B2
(45) Date of Patent: Jun. 9, 2015

(54) METHOD FOR MONITORING FERTILITY BY MEASURING THE CONCENTRATION OF HORMONES IN TEARS

(75) Inventors: Fiona Patricia Carney, Atlanta, GA (US); Carol Ann Morris, Duluth, GA (US)

(73) Assignee: Novartis AG, Basel (CH)

( * ) Notice: Subject to any disclaimer, the term of this patent is extended or adjusted under 35 U.S.C. 154(b) by 1277 days.

(21) Appl. No.: 11/787,681

(22) Filed: Apr. 17, 2007

(65) Prior Publication Data

US 2007/0197931 A1  Aug. 23, 2007

Related U.S. Application Data

(63) Continuation of application No. 10/797,678, filed on Mar. 10, 2004, now abandoned.

(60) Provisional application No. 60/454,177, filed on Mar. 13, 2003.

(51) Int. Cl.
*A61B 5/00* (2006.01)
*A61B 5/145* (2006.01)
*A61B 10/00* (2006.01)
*A61B 5/1455* (2006.01)

(52) U.S. Cl.
CPC . *A61B 5/42* (2013.01); *A61B 5/145* (2013.01); *A61B 5/14532* (2013.01); *A61B 5/14546* (2013.01); *A61B 5/1455* (2013.01); *A61B 5/4306* (2013.01); *A61B 10/0012* (2013.01); *A61B 10/0045* (2013.01); *A61B 2010/0067* (2013.01)

(58) Field of Classification Search
CPC ............... A61B 5/145; A61B 5/14546; A61B 10/0012; A61B 10/0045; A61B 5/42; A61B 5/14532; A61B 5/1455; A61B 2010/0067; A61B 5/4306

USPC ........... 600/551, 558, 584; 435/806; 436/906; 604/294
See application file for complete search history.

(56) References Cited

U.S. PATENT DOCUMENTS

| 4,658,833 | A | 4/1987 | Stuart | 128/771 |
| 6,020,139 | A * | 2/2000 | Schwartz et al. | 506/7 |
| 6,451,619 | B1 | 9/2002 | Catt et al. | 436/514 |
| 6,451,871 | B1 | 9/2002 | Winterton et al. | 523/106 |
| 6,596,701 | B1 * | 7/2003 | Schwartz et al. | 514/46 |
| 2002/0049374 | A1 | 4/2002 | Abreu | 600/405 |
| 2002/0111561 | A1 | 8/2002 | Kaga | 600/551 |
| 2003/0045783 | A1 | 3/2003 | March et al. | 600/319 |

FOREIGN PATENT DOCUMENTS

EP  0 703 454  12/2001

OTHER PUBLICATIONS

International Search Report.

* cited by examiner

*Primary Examiner* — Sean Dougherty
(74) *Attorney, Agent, or Firm* — Sheng-Hsin Hu; Jian Zhou

(57) ABSTRACT

The invention provides methods and kits for monitoring the status of women's health, including HRT monitoring and determination or diagnosis of ovulation, contraception, pregnancy, menopause, polycystic ovarian disease, and female sexual dysfunction. The method comprises the steps of: (a) collecting a tear fluid from a female human; (b) determining the tear concentration of at least one hormone of relevance to female fertility, sexual differentiation or sexual dysfunction in a female human, wherein the tear concentration is diagnostics of the status of women's health.

20 Claims, 2 Drawing Sheets

METHOD FOR MONITORING FERTILITY BY MEASURING THE CONCENTRATION OF HORMONES IN TEARS

This application is a continuation of U.S. patent application Ser. No. 10/797,678, filed Mar. 10, 2004 now abandoned, which claims the benefit under USC §119 (e) of U.S. Provisional Application No. 60/454,177 filed Mar. 13, 2003, incorporated by reference in its entirety.

The invention is related to a method and kits for monitoring women's health by analyzing analytes of relevance to fertility, sexual differentiation and/or sexual dysfunction. In particular, the invention is related to a method for monitoring the fertility status of an individual subject, a birth control method, a method for menopausal diagnosis, a method for monitoring hormone therapy, a method for diagnosing/monitoring polycystic ovarian disease. In addition, the invention provides kits for monitoring women's health by analyzing analytes of relevance to fertility, sexual differentiation in tears and sexual dysfunction.

BACKGROUND OF THE INVENTION

It is important to detect/measure one or more particular hormones in serum, for a variety of reasons, such as, for example, for assisting in diagnosing the occurrence of an endocrinological disorder, for monitoring the amount of hormones required in hormonal replacement therapy, or for assessing ovulation, pregnancy, contraception, menopause or sexual dysfunction of an individual. Historically, blood collection was required to gather information on the physiological properties of the body, including monitoring women's reproductive cycle. Blood collection is an invasive technique requiring arterial or venous puncture. A patient has to endure discomfort associated with needles or other devices to obtain blood samples for testing. In addition, blood collection sometimes can be associated with problems in various ethnic settings. Therefore, assays of serum hormones are preferably avoided or replaced by alternative non-invasive assays.

In the last decade, considerable attention was paid to substitute assays of serum analytes of interest with assays of urinary analytes of interest. For example, a number of patents and patent applications disclose non-invasive home use fertility tests based on urine analysis (see, for example, U.S. Pat. No. 6,399,398; EP0236023A2; EP0656118B1; EP0703454B1; EP0745853B1; EP0745854B1; EP0728310B1). Those fertility tests are largely based on a series of concentration measurements of urinary estradiol metabolites (e.g., estrone-3-glucuronide, estradiol-3-glucuronide, estradiol-17-glucuronide, estriol-3-glucuronide, estriol-16-glucuronide), urinary luteinising hormone (LH), and/or urinary pregnanediol-3-glucuronide (P3G) (i.e., a progesterone metabolite). To be useful, such concentration data must be determined accurately, usually from a series of samples. For example, a sample may need to be collected daily over an extended sequence of days, and successive daily analyte concentrations are compared to identify a significant concentration change indicative of a change in fertility (ie. fecundity) status. However, there is a natural variation in body fluid source concentration (i.e., "biological concentration variability") that can interfere with the comparability of such urinary concentration data. The sample to be assayed is collected while urine is being excreted. When the collected sample is analyzed for the presence of a specific analyte, such as an estradiol metabolite, the apparent concentration of the analyte may not be a true reflection of the amount of analyte being produced by the body at that time (i.e., may not be correlated with the serum concentration of the analyte under analysis). The degree of fluid intake, and kidney function, has a very significant influence on the actual volume and frequency of urine excretion and consequently the concentration of the analyte. If fluid intake has been relatively high, or relatively low, during the previous few hours, the measurable concentration of analyte in the collected sample can be much lower (or higher) than normal, leading to inaccurate and possibly misleading information. Additionally, diurnal hormone variations are affected by aging, sleep loss, night or shift work, physical exercise, jet lag, affective disorders and endocrine diseases.

Therefore, there is a need for a non-invasive method of assaying an analyte of relevance to fertility in an alternative body fluid in a constant and more accurate manner.

SUMMARY OF THE INVENTION

One object of the invention is to provide a method for assaying one or more analytes of relevance to fertility in a body fluid. Such method not only has a relatively high sensitivity and reliability for estimating the period of peak fertility in the human menstrual cycle for the purposes of natural contraceptive practice and fertility enhancement, but also are suitable for patients to be performed in a more convenient and discreet manner (e.g., at home, or at an office).

Another object of the invention is to provide a reliable method and kits for monitoring ovulation, pregnancy, contraception, menopause or sexual dysfunction.

A further object of the invention is to provide user-friendly kits for assaying one or more analytes of significance in relation to female fertility and sexual differentiation in a body fluid. Such kits can be used in a fertility test to provide reliable information concerning fertility status as an aid to birth control or to fertility enhancement. Such kits can also be used in pregnancy tests and diagnosis of menopause or sexual dysfunction.

These and other objects of the invention are met by the various aspects of the invention described herein.

The invention, in one aspect, provides a method for determining the fertility status of a current ovulation cycle of a female human, comprising the steps of: (a) monitoring variation in tear concentration of at least one hormone of relevance to female fertility; and (b) evaluating the correspondence of the variation in tear concentration of said hormone to onset of the transition phase, fertile phase, ovulation, or infertile phase of a menstrual cycle in said female human, wherein the step of monitoring is performed by periodically collecting a tear fluid from the female human and then determining the tear concentration of said hormone.

The invention, in another aspect, provides a method for determining the fertility status of a current ovulation cycle of a female human, comprising a series of steps performed at least once per day for at least several days preceding and following ovulation, said steps comprising: (a) collecting a tear fluid from the female human; (b) determining variation in tear concentration of at least one hormone of relevance to female fertility to establish variation in tear concentration of said hormone; and (c) evaluating the correspondence of the variation in tear concentration of said hormone to onset of the fertile phase, ovulation, or infertile phase of a menstrual cycle in said female human.

The present invention, in still another aspect, provides a birth control method, comprising the steps of: (a) monitoring variation in tear concentration of at least one hormone of relevance to female fertility; (b) evaluating the correspondence of the variation in tear concentration of said hormone to onset of the fertile phase, ovulation, and/or terminal infertile period of a menstrual cycle in said female human; and (c) causing said female human to avoid exposure to fertilization beginning at least at the onset of the fertile phase and ending day "+2" relative to the day of actual ovulation, wherein the step of monitoring is performed by periodically collecting a tear fluid from the female human and then determining the tear concentration of said hormone.

The invention, in a further aspect, provides a birth control method, comprising a series of steps performed at least once per day for at least several days preceding and following ovulation, said steps comprising: (a) collecting a tear fluid from the female human; (b) determining variation in tear concentration of at least one hormone of relevance to female fertility to establish variation in tear concentration of said hormone; (c) evaluating the correspondence of the variation in tear concentration of said hormone to onset of the fertile phase, ovulation, and/or terminal infertile period of a menstrual cycle in said female human; and (c) causing said female human to avoid exposure to fertilization beginning at least at the onset of the fertile phase and ending day "+2" relative to the day of actual ovulation.

The invention, in another further aspect, provides a method for monitoring the status of women's health, comprising the steps of: (a) collecting a tear fluid from the female human; (b) determining the tear concentration of at least one hormone of relevance to female fertility, sexual differentiation or sexual dysfunction in a female human, wherein the tear concentration is diagnostics of the status of women's health.

The invention, in a still further aspect, provides a method for determining the fertility status of a current ovulation cycle of a female non-human mammal, comprising the steps of: (a) monitoring variation in tear concentration of at least one hormone of relevance to female fertility; and (b) evaluating the correspondence of the variation in tear concentration of said hormone to onset of the transition phase, fertile phase, ovulation, or infertile phase of a menstrual cycle in said nonhuman female animal, wherein the step of monitoring is performed by periodically collecting a tear fluid from the nonhuman female animal and then determining the tear concentration of said hormone.

The invention further provides kits for determining the fertility status of a current ovulation cycle of a female human, for birth control, and for monitoring the status of women's health. A kit of the invention comprises a plurality of tear-collecting devices, a testing reagent composition which specifically reacts or interacts with at least one hormone of relevance to female fertility, sexual differentiation or sexual dysfunction in a female human to form a detectable signal which changes in a concentration-dependent manner, and optionally instruction.

These and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF PREFERRED EMBODIMENTS

Figure 1A:
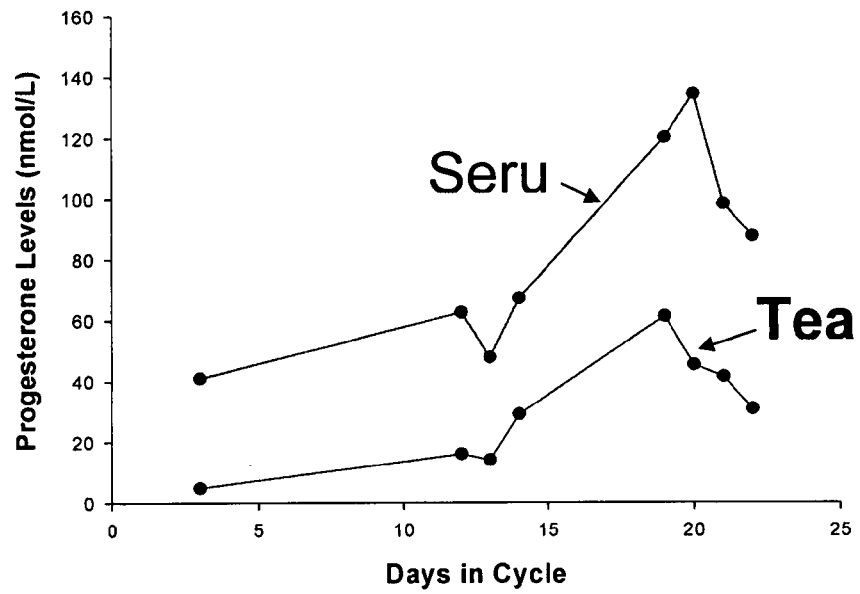
FIG. 1A shows correlation of progesterone in tears and serum of patient A.

Reference now will be made in detail to the embodiments of the invention, one or more examples of which are set forth below. Each example is provided by way of explanation of the invention, and is not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. As employed throughout the disclosure, the following terms, unless otherwise indicated, shall be understood to have the following meanings.

The term "analyte" refers to a substance being tested. Exemplary analytes of interest include, but are not limited to, hormones of relevance to female fertility, sexual differentiation an/or sexual dysfunction, and metabolites thereof. Exemplary hormones of relevance to female fertility, sexual differentiation an/or sexual dysfunction include, without limitation, estrogens (such as, for example, estradiol, estriol and estrone), progesterone, luteinising hormone (LH), follicle stimulating hormone (FSH), testosterone, human chorionic gonadotropin (hCG) sex hormone binding globulin, prolactin and the like.

"Biological concentration variability" refers to variation in analyte concentration in a body fluid, derived from variation in the volume of a body fluid (e.g., urine or a tear fluid) which is produced and/or secreted under different physiological and environmental conditions. For example, when collecting a tear fluid from the eye of a user using a glass capilary tube, a relatively large quantity of tear (i.e., reflex tear) is produced/secreted by the eye and therefore the apparent concentration of the analyte may not be a true reflection of the amount of analyte being produced by the body at that time (i.e., may not be correlated with the serum concentration of the analyte under analysis). Such biological concentration variability can interfere with the comparability of such tear or urine concentration data.

The "fertile phase or period" refers to the portion of the ovulation cycle (i.e., menstrual cycle), from day "−3" up to and including day "+3" relative to the day of actual ovulation. During the fertile phase, it is most likely that intercourse will result in fertilization, because of the normal viability of spermatozoa and ova. Ovulation day can be accurately pinpointed by measurement of, for example, serum LH levels, taking ovulation to occur in 12-48 hours following LH maximum serum concentration.

The "LH surge" refers to the dramatic (or significant) rise in LH concentration that precedes the event of ovulation.

The "LH maximum" or "LH max" refers to the peak concentration of LH.

The "transition phase or period" refers to the portion of the ovulation cycle, from day "−8" up to and including day "−4" relative to the day of actual ovulation. During the transition phase, warning of ovulation is required if the monitoring method is to provide a safe basis for contraceptive purposes.

The "infertile phase or period" refers to the portion of the ovulation cycle, from the onset of menses up to and including day "−9" relative to the day of actual ovulation.

A "significant increase in tear hormone concentration" refers to at least a 1.5 fold, preferably at least a 2 fold, more preferably 3 fold increase in tear hormone concentration as compared to its base level immediately following menses, in the period from day "+4" relative to the day of actual ovulation up to and including day 6 calculated from the onset of menses.

The term "contact lens" employed herein in a broad sense and is intended to encompass any hard or soft lens used on the eye or ocular vicinity for vision correction, diagnosis, sample collection, drug delivery, wound healing, cosmetic appearance (e.g., eye color modification), or other ophthalmic applications.

"Ophthalmically compatible", as used herein, refers to a material or surface of a material which may be in intimate contact with the ocular environment for an extended period of time without significantly damaging the ocular environment and without significant user discomfort. Thus, an ophthalmically compatible contact lens will not produce significant corneal swelling, will adequately move on the eye with blinking to promote adequate tear exchange, will not have substantial amounts of protein or lipid adsorption, and will not cause substantial wearer discomfort during the prescribed period of wear.

"Ocular environment", as used herein, refers to ocular fluids (e.g., tear fluid) and ocular tissue (e.g., the cornea) which may come into intimate contact with a contact lens.

A "hydrogel material" refers to a polymeric material which can absorb at least 10 percent by weight of water when it is fully hydrated. Generally, a hydrogel material is obtained by polymerization or copolymerization of at least one hydrophilic monomer in the presence of or in the absence of additional monomers and/or macromers. Exemplary hydrogels include, but are not limited to, poly(vinyl alcohol) (PVA), modified polyvinylalcohol (e.g., as nelfilcon A), poly(hydroxyethyl methacrylate), poly(vinyl pyrrolidone), PVAs with polycarboxylic acids (e.g., carbopol), polyethylene glycol, polyacrylamide, polymethacrylamide, silicone-containing hydrogels, polyurethane, polyurea, and the like. A hydrogel can be prepared according to any methods known to a person skilled in the art.

A "monomer" means a low molecular weight compound that can be polymerized.

Low molecular weight typically means average molecular weights less than 700 Daltons.

A "hydrophilic vinylic monomer" refers to a monomer which as a homopolymer typically yields a polymer that is water-soluble or can absorb at least 10 percent by weight water.

A "macromer" refers to medium and high molecular weight compounds or polymers that contain functional groups capable of further polymerization. Medium and high molecular weight typically means average molecular weights greater than 700 Daltons.

"Polymer" means a material formed by polymerizing one or more monomers.

"Surface modification", as used herein, means that an article has been treated in a surface treatment process (or a surface modification process), in which, by means of contact with a vapor or liquid, and/or by means of application of an energy source (1) a coating is applied to the surface of an article, (2) chemical species are adsorbed onto the surface of an article, (3) the chemical nature (e.g., electrostatic charge) of chemical groups on the surface of an article are altered, or (4) the surface properties of an article are otherwise modified. Exemplary surface treatment processes include, but are not limited to, a surface treatment by energy (e.g., a plasma, a static electrical charge, irradiation, or other energy source), chemical treatments, the grafting of hydrophilic monomers or macromers onto the surface of an article, and layer-by-layer deposition of polyelectrolytes. A preferred class of surface treatment processes are plasma processes, in which an ionized gas is applied to the surface of an article. Plasma gases and processing conditions are described more fully in U.S. Pat. Nos. 4,312,575 and 4,632,844, which are incorporated herein by reference. The plasma gas is preferably a mixture of lower alkanes and nitrogen, oxygen or an inert gas.

"LbL coating", as used herein, refers to a coating that is not covalently attached to a contact lens and is obtained through a layer-by-layer ("LbL") deposition of polyionic or charged materials on an article.

The term "bilayer" is employed herein in a broad sense and is intended to encompass: an LbL coating structure formed on a contact lens by alternatively applying, in no particular order, one layer of a first polyionic material (or charged material) and subsequently one layer of a second polyionic material (or charged material) having charges opposite of the charges of the first polyionic material (or the charged material); or a coating structure formed onto a contact lens by alternatively applying, in no particular order, one layer of a first charged polymeric material and one layer of a non-charged polymeric material or a second charged polymeric material. It should be understood that the layers of the first and second coating materials (described above) may be intertwined with each other in the bilayer.

A contact lens having a core material and an LbL coating, which comprises at least one layer of a charged polymeric material and one layer of a non-charged polymeric material that can be non-covalently bonded to the charged polymeric material, can be prepared according to a method disclosed in a co-pending U.S. application, U.S. Ser. No. 60/409,950, entitled "LbL-COATED MEDICAL DEVICE AND METHOD FOR MAKING THE SAME", filed on Sep. 11, 2002, herein incorporated by reference.

As used herein, "asymmetrical coatings" on a contact lens refers to the different coatings on the first surface and the opposite second surface of the contact lens. As used herein, "different coatings" refers to two coatings that have different surface properties or functionalities.

An "innermost layer", as used herein, refers to the first layer of an LbL coating, which is applied onto the surface of a contact lens.

A "capping layer", as used herein, refers to the last layer of a coating material which is applied onto the surface of a contact lens.

A "polyquat", as used herein, refers to a polymeric quaternary ammonium group-containing compound.

A "charged polymeric material" or a "polyionic material" refers to a charged polymer that has a plurality of charged groups in a solution, or a mixture of charged polymers each of which has a plurality of charged groups in a solution. Exemplary charged polymers includes polyelectrolytes, p- and n-type doped conducting polymers. Charged polymeric materials include both polycationic (having positive charges) and polyanionic (having negative charges) polymeric materials.

As used herein, "increased adsorption of an analyte" in reference to a contact lens having surface charges means that the contact lens with surfaces charges can bind a higher amount of the analyte of interest compared with a contact lens made of similar material and essentially free of surface charges. The contact lens with surface charges can the analyte of interest in an amount which is preferably at least about 25%, more preferably at least about 50%, even more preferably at least about 75% higher than the amount of the analyte of interest bound by a contact lens made of similar material and essentially free of surface charges The term "receptor" employed herein in a broad sense and is intended to encompass, for example, a protein or fragment thereof or a chemical compound that is capable of binding said analyte in a sample. Exemplary receptors include, without limitation, antibodies or fragments thereof, lectins or fragments thereof, hormone receptors or fragments thereof, drug receptors or fragment thereof, enzymes or fragment thereof, aptamers, nucleic acids, nucleic acid analogs, and the like.

The invention is directed to methods and kits for monitoring ovulation, pregnancy, contraception, menopause or sexual dysfunction by determining the concentration of at least one hormone or metabolite thereof, of relevance to female fertility, sexual differentiation an/or sexual dysfunction, and metabolites thereof, in a tear fluid. The invention is based in part on the discovery that there exists a direct correlation between serum and tear concentrations of hormones of significance in relation to the fertility status of a female and/or to sex differentiation or dysfunction. Three hormones of relevance to the female fertility, estradiol, progesterone and luteinising hormone (LH) have been examined. In addition, testosterone is also investigated.

The results indicate that the concentrations of steroid hormones, estradiol and progesterone, in tears are very similar to their corresponding serum concentrations at any time points during one menstrual cycle while the concentration of LH in tears are approximately 5 fold lower than serum concentration. Based on such correlation between the ocular concentration (i.e., in tears) and serum concentration of hormones of significance in relation to female fertility and sexual differentiation, one can collect tear samples and determine the concentration of one or more hormones of significance in relation to female fertility and sexual differentiation to monitor/assess ovulation, pregnancy, contraception, menopause or sexual dysfunction.

The detection and measurement of estradiol is of great importance in the area of fertility testing. The ovary elaborates three estrogen compounds; estradiol, estriol and estrone. Estradiol is the most potent estrogen and is readily oxidized to estrone by the body. Estrone is hydroxylated to form estriol. Estradiol is secreted by the ovary and placenta. It is synthesized by the aromatization of androgens in the thecal and granulosa cells of the ovary and placenta. The aromatization is stimulated by follitropin (FSH). Estradiol synthesis in turn stimulates production of lutropin (LH) receptors necessary for the synthesis of adrogen precursors.

Estradiol is important for female sexual differentiation during gestation, sexual development at the onset of puberty, and regulation of the menstrual cycle. The menstrual cycle is the result of a precise coordination of the functional characteristics of the central nervous system, the hypothalamus, the pituitary, the ovary, and the endometrium, which regulate the cyclic release of Gonadotropin Releasing Hormone (GnRH), luteinizing hormone (LH) and follicle stimulating hormone (FSH), and ovarian steroids (estradiol and progesterone). Estradiol is involved in both the stimulation and inhibition of the release of the gonadotropins, exerting both a positive and a negative feedback. Early in the follicular phase, ovarian secretion of estradiol from the thecal and granulosa cells is modest. During the follicular phase, estradiol stimulates endometrial growth (repairing the endometrium after menses). Toward mid-cycle, LH production increases and results in the release of the ovum by the rupture of the developed follicle. After ovulation, estradiol secretion declines slightly. During the luteal phase, estradiol along with progesterone are secreted by the corpus luteum, stimulating further endometrial growth. If the ovum is not fertilized, there is a further drop in estradiol and progesterone. This drop in estradiol and progesterone initiates menses.

The measurement of estradiol is important for the evaluation of normal sexual development (menarche), causes of infertility (anovulation, amenorrhea, dysmenorrhea), and menopause. Normal estradiol levels are lowest at menses and during the early follicular phase (25-75 pg/mL). The levels rise in the late follicular phase to a peak of 200-600 pg/mL just before the LH surge initiates ovulation. As LH peaks, estradiol begins to decrease before rising again during the luteal phase (100-300 pg/mL). If conception does not take place, estradiol falls further to its lowest levels, thus initiating menses. If conception occurs, estradiol levels continue to rise, reaching levels of 1-5 ng/mL during the first trimester, 5-15 ng/mL during the second trimester, and 10-40 ng/mL during the third trimester. During menopause, estradiol levels remain low.

The detection and measurement of progesterone (4-pregnen-3,20-dione) is of great importance in the area of assessing the occurrence of ovulation, conception, the risk of abortion, or ectopic pregnancy.

In the mitochondria, cholesterol is first converted to pregnenolone via a cytochrome P-450 enzyme-dependent side chain cleavage followed by hydroxylation. Pregnenolone is then converted to progesterone in a reaction catalyzed by 3.beta.-hydroxysteroid dehydrogenase and isomerase enzymes (3β-HSD). Progesterone is produced primarily by the corpus luteum of the ovary in normally menstruating women and to a lesser extent by the adrenal cortex. At approximately the sixth week of pregnancy, the placenta becomes the major producer of progesterone. In the circulation of blood, approximately 97-98% of the progesterone is bound to albumin or Cortisol Binding Protein. Progesterone is metabolized, primarily in the liver, to pregnanediol and its water soluble sulfate and glucuronide derivatives and excreted in the urine.

The major functions of progesterone are in the preparation of the uterus for implantation and maintaining pregnancy. During the follicular phase, progesterone levels remain low (0.2-1.5 ng/mL). Following the LH surge and ovulation, luteal cells in the ruptured follicle produce progesterone in response to LH. During the luteal phase, progesterone rises rapidly to a maximum of 10-20 ng/mL at the fifth to seventh day following ovulation. If pregnancy does not occur, progesterone levels decrease during the last four days of the menstrual cycle due to the regression of the corpus luteum.

If conception occurs, the levels of progesterone are maintained at mid-luteal levels by the corpus luteum until about the sixth week. At that time the placenta becomes the main source of progesterone and levels rise from approximately 10-50 ng/mL in the first trimester to 50-280 ng/mL in the third trimester.

Serum progesterone is a reliable indicator of either natural or induced ovulation because of its rapid rise following ovulation. Disorders of ovulation, including anovulation, are relatively frequent and are responsible for infertility in approximately 15 to 20% of patients. Progesterone levels are abnormally low in these patients during the mid-luteal phase.

Luteal phase deficiency is a reproductive disorder associated with infertility and spontaneous abortion. It is thought to occur in 10% of infertile women. It is believed that infertility and pregnancy wastage associated with this disorder are caused by inadequate maturation and development of the endometrium. The failure of the endometrium is thought to be attributable to insufficient progesterone production by the corpus luteum. Serum progesterone levels in the luteal phase are lower than normal in women with luteal phase deficiency.

Measurement of progesterone in the first ten weeks of gestation has been shown to be a reliable predictor and an effective tool for the diagnosis and treatment of patients with threatened abortion and ectopic pregnancy. Suppressed progesterone levels (10-15 ng/mL) in the presence of detectable amounts of human chroionic gonadotropin (hCG) is highly suggestive of threatened abortion or ectopic pregnancy, regardless of gestational age.

Typical physiological levels (ng/mL) of serum progesterone in human are as follows.

| Women Normal Cycling: | |
|---|---|
| Follicular | 0.5 |
| Ovulatory | 0.5-1.5 |
| Luteal | 4.0-20.0 |
| Other: | |
| Prepubertal | 0.2-0.5 |
| Postmenopausal | 0.5 |
| Pregnancy | 40-200 |
| Men | |
| Prepubertal | 0.25 |
| Adult | 0.25 |

The detection and measurement of LH is of great importance in the area of fertility testing. LH is secreted by the anterior lobe of the pituitary gland, which stimulates ovulation, the development of the corpus luteum with its subsequent secretion of progesterone in females, and the development of interstitial tissue. The concentration of LH dramatically rises preceding the event of ovulation and peaks in blood one to two days before ovulation, at the onset of the most fertile period in a menstrual cycle. Such dramatic rise in LH concentration is often referred to "LH surge". Once the LH surge has been detected in an individual, it can be said that ovulation of that individual is imminent. Also, the day of the cycle on which ovulation has occurred can be noted for future reference. If the LH surge is detected, and hence the day of ovulation accurately pinpointed, it can be indicated to an individual with a very high degree of certainty that the individual will no longer be fertile four days hence (3 days after ovulation). The length of the LH surge is highly variable, lasting between 10 and 31 hours in about half of the women, less than 10 hours in 38 percent of women, and more than 31 hours in 12 percent of women.

The detection and measurement of testosterone is of great importance in diagnosis of polycystic ovary syndrome (PCOS) or polycystic ovary disease (PCOD). PCOS is a common endocrine condition which affects women of reproductive age. Anovulation, menstrual irregularities, hirsutism, and infertility are common clinical presentations. Long-term health concerns such as type 11 diabetes mellitus and, possibly, cardiovascular disease, have been linked to PCOS. PCOS is very often associated with insulin resistance (IR) and hyperinsulinemia (hyper 1). From in vitro and vivo studies and treatment of hyper 1, it has been shown that the hyper I of PCOS stimulates androgen production. It is believed that hyper I of PCOS stimulates androgen production: by first provoking an important decrease of the sex hormone binding globulin (SHBG) thus increasing the free, bioactive testosterone level and then by activating the cytochrome P 450 c 17 alpha enzymatic system that controls androgen production. Currently, PCOS is diagnosed by the finding of chronic anovulation and hyperandrogenism characterized by a high serum level of free testosterone.

Any tear-collecting device known to a person skilled in the art can be used in collecting of tear fluids. Examples of tear-collecting devices are glass capillary tubes, hydrogel strips, and contact lenses. A tear-collecting device is preferably a hydrogel strip, more preferably a contact lens, even more preferably a contact lens capable of binding one or more hormones of relevance to female fertility, sexual differentiation an/or sexual dysfunction, and metabolites thereof.

In accordance with the present invention, a hydrogel strip as a tear-collecting device is one disclosed in a copending U.S. patent application Ser. No. 60/415,914, entitled "Methods and Kits For Assays Of Analytes Of Interest In Tears", filed on Oct. 3, 2002, herein incorporated by reference in its entirety. The hydrogel strip is made of a hydrogel material in substantially dry state and has a uniform cross-section, wherein said strip is characterized by having a substantially uniform swelling along the hydrogel strip when fully wicked by a tear fluid and characterized by having a defined correlation between the volume of tear uptake by said strip and the length of the tear-wicked end portion of said strip.

A hydrogel strip as a tear-collecting device can offer some advantages over a glass capillary tube. First, it is much easier to handle a hydrogel strip than to handle a glass capillary tube. A glass capillary tube may break and potentially cause injury during handling and transportation. Liquid contained in a glass capillary tube can be spilled (or dropped) by accident to cause some health or environmental concerns. In contrast, a hydrogel strip is not fragile. Once a tear fluid is absorbed, it is confined by the hydrogel strip so that problems associated with spilling out of liquid is eliminated or at least minimized. Second, it is safer, much faster, and less irritating to use a hydrogel strip than to use a glass capillary tube in collecting tear fluids. Capillary tubes are generally hard and relatively sharp because of their small cross-section dimension and their thin walls. However, hydrogels are soft, especially when hydrated (i.e., after absorbing some tear fluid) and have been widely used in contact lenses. Compared with a glass capillary tube, a hydrogel strip is less likely to cause damage to an eye and can be used by a person who is not a well trained professional. Furthermore, assays for one or more analytes of interest can be carried out directly on and in one or more divided pieces of the tear-wicked portion of a hydrogel strip. Or, a tear fluid absorbed by a hydrogel strip can be substantially recovered by a method known to a person skilled in the art, for example, including centrifuging, vacuum, squeezing and the like.

Any known, suitable hydrogels can be used in the invention. Exemplary hydrogels include, but are not limited to, poly(vinyl alcohol) (PVA), modified polyvinylalcohol (e.g., as nelfilcon A), poly(hydroxyethyl methacrylate), poly(vinyl pyrrolidone), PVAs with polycarboxylic acids (e.g., carbopol), polyethylene glycol, polyacrylamide, polymethacrylamide, silicone-containing hydrogels, polyurethane, polyurea, and the like. A hydrogel can be prepared according to any methods known to a person skilled in the art.

A hydrogel strip can have any dimension suitable for collecting tear fluids. A hydrogel strip of the invention has a length sufficient long to absorb a minimum volume of tear (e.g., at least about 1 µl). A hydrogel strip is preferably at least 15 mm in length, more preferably at least 30 mm in length.

Preferably, the dimension of the cross-section (e.g, diameter, width, height, etc.) of a hydrogel strip is neither too small nor too large. Where the dimension of the cross-section of a hydrogel strip is too small, the hydrogel strip becomes not structurally steady and/or can become sharp so that it can potentially cause damages to eye tissues. Where the dimension of the cross-section of a hydrogel strip is too large, the hydrogel strip can not access the lateral canthus.

A hydrogel strip preferably has a uniform cross-section along the strip. The cross-section of a hydrogel strip of the invention can have any geometric shape, for example, such as rectangular, square, circular, triangular, annular ring, or the like. Preferably, the cross-section of a hydrogel strip has a rectangular shape. The rectangular cross-section has a width of from about 1 mm to about 3 mm, preferably from 1.5 mm to 2 mm, and a height of from 0.5 mm to 1.5 mm, preferably from 0.8 mm to 1.2 mm. Where the cross-section of a hydrogel strip of the invention is circular, the diameter of the circular cross-section is preferably from 1 mm to 3 mm, more preferably from 1.5 mm to 2.2 mm.

A "substantially uniform swelling along the hydrogel strip when fully wicked by a tear fluid" means that when a hydrogel strip is fully wicked by a fluid (e.g., a tear), it has a substantially uniform increase in volume along the length of the hydrogel strip and no significant change in the geometric shape of the strip can be observed.

Correlation between the volume of fluid (e.g., tear) uptake by said strip and the length of the fluid-wicked end portion of said strip preferably is a substantially linear relationship. With a substantially linear correlation, the volume of tear uptake by a hydrogel strip can be easily quantified. In a preferred embodiment, the volume of tear uptake is noticeably marked on a hydrogel strip.

For example, a hydrogel strip is prepared from poly(vinyl alcohol) (PVA) and has a dimension of 1.5 mm in width, 1.0 mm in height, and 30 mm in length.

In accordance with the present invention, a contact lens as a tear-collecting device is preferably a soft contact lens, more preferably a hydrogel soft contact lens, even more preferably a daily disposable hydrogel soft contact lens (for example, DAILIES® lenses). For the purpose of collecting a tear fluid, a contact lens is wore preferably for at least 30 minutes, more preferably for at least 2 hours, even more preferably for at least 4 hours, much more preferably for at least 6 hours. It is believed that during the period immediately after placing the contact lens onto the cornea of an eye of a user, a relatively large amount of reflex tear can be secreted by the eye and the tear flow in the eye can increase significantly and that after at least 30 minutes of wearing, the production of reflex tear may decrease, the tear flow in the eye may be restored back to the normal state, and the distribution of analytes in the contact lens and the ocular fluid may be in an equilibrium state.

A contact lens as a tear-collecting device can offer some advantages over a hydrogel strip. First, a contact lens can provide utilities not only for vision correction and/or cosmetic appearance (e.g., eye color modification) but also for tear collection. Second, a contact lens can minimize or eliminate "biological concentration variability" in tear fluid. In contrast, a hydrogel strip may collect in large part reflex tear, in which the apparent concentration of an analyte may not be a true reflection of the amount of that analyte being produced by the body at that time (i.e., may not be correlated with the serum concentration of the analyte under analyzed). Therefore, reliability in the comparability of tear concentration data can be enhanced by using a contact lens in collecting tears.

Preferably, a contact lens as a tear-collecting device is capable of binding the analyte of interest. Examples of such contact lenses are disclosed in a copending U.S. patent application Ser. No. 10/797,707, entitled "DEVICES FOR COLLECTING ANALYTES OF INTEREST IN TEARS", filed on the same date herewith this application, herein incorporated by reference in its entirety. In accordance with this embodiment, a contact lens comprises: (1) surface charges present in a density sufficient to impart to the contact lens an increased adsorption of the analyte of interest; (2) a coating comprising a receptor which binds specifically the analyte of interest; (3) molecular imprints for the analyte of interest; or (4) a core material that is prepared from a composition containing a receptor which binds specifically the analyte of interest. By wearing a contact lens capable of binding one or more analytes of interest, over a period of time, for example, 15 minutes or longer, preferably one hour or longer, more preferably 2 hours or longer, even more preferably 4 hours or longer, most preferably 8 hours or longer, the one or more analytes of interest can be enriched over the period of wearing time, since the tear fluid in a normal human eye is continuously replenished. By using a contact lens capable of binding an analyte of interest in a tear fluid, one can determine the concentration of an analyte of interest accumulated over a period of time and therefore the effects of biological concentration variability on the determined concentration of the one or more analytes of interest can be minimized. Therefore, the accuracy of assays for the analytes in a body fluid can be greatly enhanced.

Surface charges, either positive charges or negative charges, can be introduced on the surface of a contact lens by preparing the contact lens from a composition comprising a positively or negatively charged monomer or macromer. Any known suitable charged monomers or macromers can be used in the preparation of a contact lens of the invention.

The density of surface charges of a contact lens can be determined according to any known suitable method. Preferably, a contact lens has a surface charge density at which the contact lens can bind the analyte of interest in an amount which is at least about 25% higher than the amount of the analyte of interest bound by a contact lens made of similar material and essentially free of surface charges.

Surface charges can also be introduced on the surface of a contact lens by altering the chemical nature (i.e., electrostatic charge) of chemical groups on its surface, for example, by means of contact with a vapor or liquid, and/or by means of application of an energy source (e.g., an plasma treatment, an electron beam treatment, a corona discharge, or an X-ray treatment).

Surface charges are preferably introduced on the surface of a contact lens by applying an LbL coating composed of at least one layer of a polyionic material. Application of an LbL coating may be accomplished in a number of ways as described in U.S. Pat. No. 6,451,871 (herein incorporated by reference in its entirety) and pending U.S. patent applications Ser. Nos. 09/774,942, 09/775,104, 60/409,950), herein incorporated by reference in their entireties. One coating process embodiment involves solely dip-coating and dip-rinsing steps. Another coating process embodiment involves solely spray-coating and spray-rinsing steps. However, a number of alternatives involve various combinations of spray- and dip-coating and rinsing steps may be designed by a person having ordinary skill in the art.

For example, a solely dip-coating process involves the steps of: (a) immersing a medical device in a first coating solution of a first polyionic material; (b) optionally rinsing the medical device by immersing the medical device in a first rinsing solution; (c) immersing said medical device in a second coating solution of a second polyionic material to form a first polyelectrolyte bilayer of the first and second polyionic materials, wherein the second polyionic material has charges opposite of the charges of the first polyionic material; (d) optionally rinsing said medical device by immersing the medical device in the rinsing solution; and (e) optionally repeating steps (a) to (d) for a number of times to form additional polyelectrolyte bilayers. A thicker LbL coating can be produced by repeating steps (a) to (d) preferably for 2 to 40 times. A preferred number of bilayers is about 5 to about 20 bilayers. While more than 20 bilayers are possible, it has been found that delamination may occur in some LbL coatings having an excessive number of bilayers.

The immersion time for each of the coating and rinsing steps may vary depending on a number of factors. Preferably, immersion of the core material into the polyionic solution occurs over a period of about 1 to 30 minutes, more preferably about 2 to 20 minutes, and most preferably about 1 to 5 minutes. Rinsing may be accomplished in one step, but a plurality of rinsing steps can be quite efficient.

Another embodiment of the coating process is a single dip-coating process as described in U.S. application Ser. No. 09/775,104, herein incorporated by reference in its entirety. Such single dip-coating process involves dipping a core material of a medical device in a solution containing a negatively charged polyionic material and a positively charged polyionic material in an amount such that the molar charge ratio of said solution is from about 3:1 to about 100:1. Multiple bilayers can be formed on a medical device by using this single dip-coating process.

Another embodiment of the coating process involves a series of spray coating techniques. For example, a solely spray-coating process generally includes the steps of: (a) spraying a medical device with a first coating solution of a first polyionic material; (b) optionally rinsing the medical device by spraying it with a rinsing solution; (c) spraying said medical device with a second coating solution of a second polyionic material to form a first polyelectrolyte bilayer of the first and second polyionic materials, wherein the second polyionic material has charges opposite of the charges of the first polyionic material; (d) optionally rinsing said medical device by spraying it with the rinsing solution; (e) optionally repeating steps (a) to (d) for a number of times. A thicker LbL coating can be produced by repeating steps (a) to (d) preferably for 2 to 40 times.

The spray coating application may be accomplished via a process selected from the group consisting of an air-assisted atomization and dispensing process, an ultrasonic-assisted atomization and dispensing process, a piezoelectric assisted atomization and dispensing process, an electromechanical jet printing process, a piezo-electric jet printing process, a piezo-electric with hydrostatic pressure jet printing process, and a thermal jet printing process; and a computer system capable of controlling the positioning of the dispensing head of the spraying device on the ophthalmic lens and dispensing the coating liquid. Those spraying coating processes are described in U.S. Application No. 60/312199, herein incorporated by reference in its entirety. By using such spraying coating processes, an asymmetrical coating can be applied to a medical device. For example, the back surface of a contact lens can be coated with a hydrophilic and/or lubricous coating material and the front surface of the contact lens can be coated with an antimicrobial material. It is also possible to produce a coating on a contact lens, the coating having a functional pattern so as to provide simultaneously multiple benefits to a wearer.

The polyionic materials that may be employed in the present invention include polyanionic and polycationic polymers. Examples of suitable polyanionic polymers include, for example, a synthetic polymer, a biopolymer or modified biopolymer comprising carboxy, sulfo, sulfato, phosphono or phosphato groups or a mixture thereof, or a salt thereof, for example, a biomedical acceptable salt and especially an ophthalmically acceptable salt thereof when the article to be coated is an ophthalmic device.

Examples of synthetic polyanionic polymers are: a linear polyacrylic acid (PAA), a branched polyacrylic acid, a polymethacrylic acid (PMA), a polyacrylic acid or polymethacrylic acid copolymer, a maleic or fumaric acid copolymer, a poly(styrenesulfonic acid) (PSS), a polyamido acid, a carboxy-terminated polymer of a diamine and a di- or polycarboxylic acid (e.g., carboxy-terminated Starburst™ PAMAM dendrimers from Aldrich), a poly(2-acrylamido-2-methylpropanesulfonic acid) (poly-(AMPS)), an alkylene polyphosphate, an alkylene polyphosphonate, a carbohydrate polyphosphate or carbohydrate polyphosphonate (e.g., a teichoic acid). Examples of a branched polyacrylic acid include a Carbophil® or Carbopol® type from Goodrich Corp. Examples of a copolymer of acrylic or methacrylic acid include a copolymerization product of an acrylic or methacrylic acid with a vinyl monomer including, for example, acrylamide, N,N-dimethyl acrylamide or N-vinylpyrrolidone.

Examples of polyanionic biopolymers or modified biopolymers are: hyaluronic acid, glycosaminoglycane such as heparin or chondroitin sulfate, fucoidan, poly-aspartic acid, poly-glutamic acid, carboxymethyl cellulose, carboxymethyl dextrans, alginates, pectins, gellan, carboxyalkyl chitins, carboxymethyl chitosans, sulfated polysaccharides.

A preferred polyanionic polymer is a linear or branched polyacrylic acid or an acrylic acid copolymer. A more preferred anionic polymer is a linear or branched polyacrylic acid. A branched polyacrylic acid in this context is to be understood as meaning a polyacrylic acid obtainable by polymerizing acrylic acid in the presence of suitable (minor) amounts of a di- or polyvinyl compound.

A suitable polycationic polymer as part of the bilayer is, for example, a synthetic polymer, biopolymer or modified biopolymer comprising primary, secondary or tertiary amino groups or a suitable salt thereof, preferably an ophthalmically acceptable salt thereof, for example a hydrohalogenide such as a hydrochloride thereof, in the backbone or as substituents. Polycationic polymers comprising primary or secondary amino groups or a salt thereof are preferred.

Examples of synthetic polycationic polymers are:
(i) a polyallylamine (PAH) homo- or copolymer, optionally comprising modifier units;
(ii) a polyethyleneimine (PEI);

(iii) a polyvinylamine homo- or copolymer, optionally comprising modifier units;
(iv) a poly(vinylbenzyl-tri-$C_1$-$C_4$-alkylammonium salt), for example a poly(vinylbenzyl-tri-methyl ammoniumchloride);
(v) a polymer of an aliphatic or araliphatic dihalide and an aliphatic N,N,N',N'-tetra-$C_1$-$C_4$-alkyl-alkylenediamine, for example a polymer of (a) propylene-1,3-dichloride or -dibromide or p-xylylene dichloride or dibromide and (b) N,N,N',N'-tetramethyl-1,4-tetramethylene diamine;
(vi) a poly(vinylpyridine) or poly(vinylpyridinium salt) homo- or copolymer;
(vii) a poly(N,N-diallyl-N,N-di-$C_1$-$C_4$-alkyl-ammoniumhalide);
(viii) a homo- or copolymer of a quaternized di-$C_1$-$C_4$-alkyl-aminoethyl acrylate or methacrylate, for example a poly (2-hydroxy-3-methacryloylpropyltri-$C_1$-$C_2$-alkylammonium salt) homopolymer such as a a poly(2-hydroxy-3-methacryloylpropyltri-methylammonium chloride), or a quaternized poly(2-dimethylaminoethyl methacrylate or a quaternized poly(vinylpyrrolidone-co-2-dimethylaminoethyl methacrylate);
(ix) polyquat; or
(x) a polyaminoamide (PAMAM), for example a linear PAMAM or a PAMAM dendrimer such as an amino-terminated Starbust™ PAMAM dendrimer (Aldrich).

The above mentioned polymers comprise in each case the free amine, a suitable salt thereof, for example a biomedically acceptable salt or in particular an ophthalmically acceptable salt thereof, as well as any quaternized form, if not specified otherwise.

Suitable comonomers optionally incorporated in the polymers according to (i), (iii), (vi) or (viii) above are, for example, hydrophilic monomers such as acrylamide, methacrylamide, N,N-dimethyl acrylamide, N-vinylpyrrolidone and the like.

Examples of polycationic biopolymers or modified biopolymers that may be employed in the bilayer of the present invention include: basic peptides, proteins or glucoproteins, for example, a poly-ε-lysine, albumin or collagen, aminoalkylated polysaccharides such as a chitosan or aminodextranes.

Particular polycationic polymers for forming the bilayer of the present invention include a polyallylamine homopolymer; a polyallylamine comprising modifier units of the above formula (II); a polyvinylamine homo- or -copolymer or a polyethyleneimine homopolymer, in particular a polyallylamine or polyethyleneimine homopolymer, or a poly(vinylamine-co-acrylamid) copolymer.

The foregoing lists are intended to be exemplary, but clearly are not exhaustive. A person skilled in the art, given the disclosure and teaching herein, would be able to select a number of other useful polyionic materials.

A receptor-containing coating can cover whole or part of the surface of a contact lens. A receptor-containing coating on a contact lens can be a layer of a receptor which is covalently attached to the contact lens. Such contact lens can be prepared by first functionalizing the surface of a preformed contact lens to obtain function groups and then covalently attaching a layer of receptor. Surface modification (or functionalization) of a medical device, for example, a contact lens, is well known to a person skilled in the art. Any known suitable method can be used.

A receptor-containing coating on a contact lens can comprise a plurality of receptors, each for a specific analyte of interest. Such contact lens can be used to collect one or more analytes of interest.

For example, the surface modification of a contact lens includes, without limitation, the grafting of monomers or macromers onto polymers to make the lens biocompatible, wherein monomers or macromers contain functional groups, for example, such as hydroxyl group, amine group, amide group, sulfhydryl group, —COOR (R and R' are hydrogen or $C_1$ to $C_8$ alkyl groups), halide (chloride, bromide, iodide), acyl chloride, isothiocyanate, isocyanate, monochlorotriazine, dichlorotriazine, mono- or di-halogen substituted pyridine, mono- or di-halogen substituted diazine, phosphoramidite, maleimide, aziridine, sulfonyl halide, hydroxysuccinimide ester, hydroxysulfosuccinimide ester, imido ester, hydrazine, axidonitrophenyl group, azide, 3-(2-pyridyl dithio)proprionamide, glyoxal, aldehyde, and epoxy.

It is well known in the art that a pair of matching functional groups can form a covalent bond or linkage under known reaction conditions, such as, oxidation-reduction conditions, dehydration condensation conditions, addition conditions, substitution (or displacement) conditions, 2+2 cyclo-addition conditions, Diels-Alder reaction conditions, ROMP (Ring Opening Metathesis Polymerization) conditions, vulcanization conditions, cationic crosslinking conditions, and epoxy hardening conditions. For example, an amino group is covalently bondable with aldehyde (Schiff base which is formed from aldehyde group and amino group may further be reduced); an hydroxyl group and an amino group are covalently bondable with carboxyl group; carboxyl group and a sulfo group are covalently bondable with hydroxyl group; a mercapto group is covalently bondable with amino group; or a carbon-carbon double bond is covalently bondable with another carbon-carbon double bond.

Exemplary covalent bonds or linkage, which are formed between pairs of crosslinkable groups, include without limitation, ester, ether, acetal, ketal, vinyl ether, carbamate, urea, amine, amide, enamine, imine, oxime, amidine, iminoester, carbonate, orthoester, phosphonate, phosphinate, sulfonate, sulfinate, sulfide, sulfate, disulfide, sulfinamide, sulfonamide, thioester, aryl, silane, siloxane, heterocycles, thiocarbonate, thiocarbamate, and phosphonamide.

Another example is amination of the surface of a medical device. If the surface of a core material has hydroxy groups, the medical device may be placed in a bath of an inert solvent, such as tetrahydrofuran, and tresyl chloride. The hydroxy groups on the surface are then tresylated. Once tresylated, the surface may be aminated in a water solution of ethylene diamine, which results in bonding the group —NH—$CH_2$—$CH_2$—$NH_2$ to the carbon atom thereon. Alternatively, for example, a contact lens made from a hydrogel, can be dipped into or sprayed with a solution containing a diaziridine compound, which is subsequently attached covalently to the surface of the contact lens via a thermal process, so as to functionalize the contact lens. Such functionalized lenses can be used in covalently attaching of a layer of a receptor.

Alternatively, for example, a contact lens made from a hydrogel, can be dipped into or sprayed with a solution containing a diaziridine compound, which is subsequently attached covalently to the surface of the contact lens via a thermal process, so as to functionalize the contact lens.

A receptor-containing coating on a contact lens can also be a coating comprising an LbL coating that is not covalently attached to the contact lens and a layer of a receptor which are covalently attached to the LbL coating through the reactive sites of the LbL coating. Such coating can be made, for example, by first applying an LbL coating to a preformed contact lens according to one of the above-described coating methods using at least one polyionic material having functional groups which will be served as reactive sites and then by covalently attaching a layer of a receptor to some of those reactive sites.

A receptor can be bound covalently to the LbL coating. This may be either a direct reaction or, preferably, a reaction in which a coupling agent is used. For example, a direct reaction may be accomplished by the use of a reagent of reaction that activates a group in the LbL coating or the receptor making it reactive with a functional group on the receptor or LbL coating, respectively, without the incorporation of a coupling agent. For example, one or more amine groups on a protein (e.g., receptor protein or antibody) may be reacted directly with isothiocyanate, acyl azide, N-hydroxysuccinimide ester, sulfonyl chloride, an aldehyde, glyoxal epoxide, 25 carbonate, aryl halide, imido ester, or an anhydride group in the LbL coating.

Alternatively, coupling agents may be used. Coupling agents useful for coupling a receptor to the LbL coating of a contact lens include, without limitation, N,N'-carbonyldiimidazole, carbodiimides such as 1-ethyl-3-(3-dimethylaminopropyl)carbodiimide ("EDC"), dicyclohexyl carbodiimide, 1-cylcohexyl-3-(2-morpholinoethyl)carbodiimide, diisopropyl carbodiimide, or mixtures thereof. The carbodiimides also may be used with N-hydroxysuccinimide or N-hydroxysulfosuccinimide to form esters that can react with amines to form amides.

Amino groups also may be coupled to the LbL coating by the formation of Schiff bases that can be reduced with agents such as sodium cyanoborohydride and the like to form hydrolytically stable amine links. Coupling agents useful for this purpose include, without limitation, N-hydroxysuccinimide esters, such as dithiobis(succinimidylpropionate), 3,3'-dithiobis(sulfosuccinimidylpropionate), disuccinimidyl suberate, bis(sulfosuccinimidyl) suberate, disuccinimidyl tartarate and the like, imidoesters, including, without limitation, dimethyl adipimate, difluorobenzene derivatives, including without limitation 1,5-difluoro-2,4 dinitrobenzene, bromofunctional aldehydes, including without limitation gluteraldehyde, and his epoxides, including without limitation 1,4-butanediol diglycidyl ether. One ordinarily skilled in the art will recognize that any number of other coupling agents may be used depending on the functional groups present in the LbL coating.

A receptor can be encapsulated in a vesicle with surfaces charges, which in turn is used to prepare an LbL coating on a contact lens, as described in a co-pending U.S. patent application No. 60/364,192, filed on Mar. 13, 2002, entitled "Materials Containing Multiple Layers of Vesicles", herein incorporated by reference in its entirety. In accordance with the present invention, vesicles include polymerized liposomes, polymerized micelles, and nanocapsules or microcapsules each having a multilayered shell of polyelectrolytes. A person skilled in the art will know how to prepare vesicles with receptor encapsulated therein.

Figure 2:
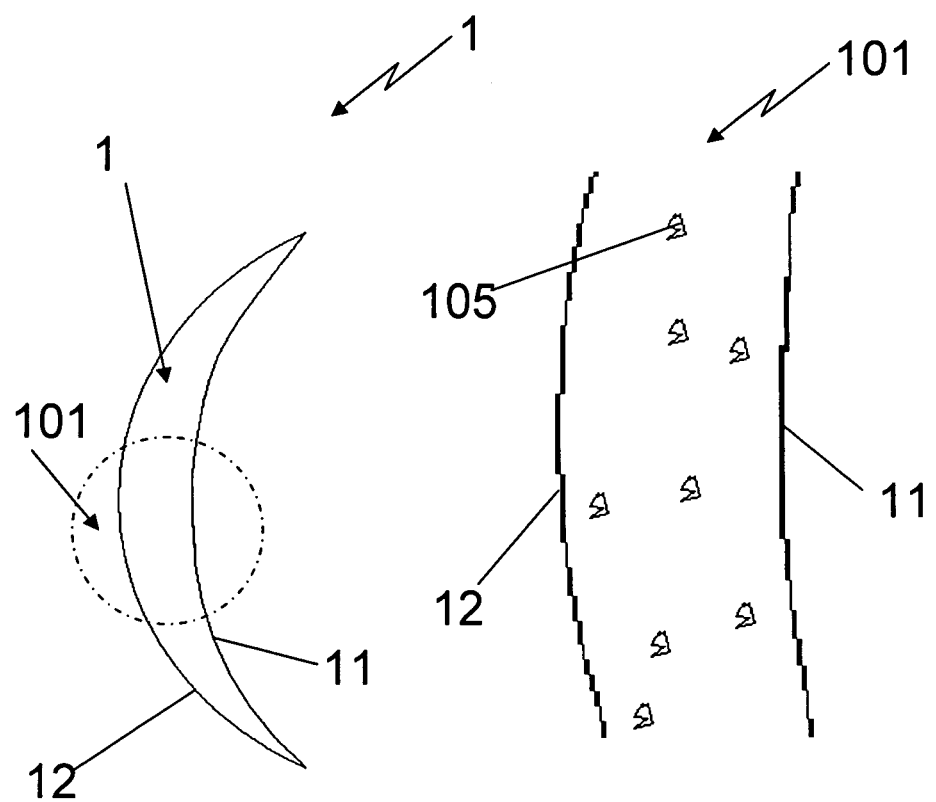
FIG. 2 schematically illustrates a sectional view of a contact lens according to a preferred embodiment of the invention.

As shown in FIG. 2, a contact lens, 1 having a concave surface 11 and a convex surface 12, which comprises molecular imprints 105 for the analyte of interest, can be, for example, made from a polymerizable composition comprising an analyte of interest. After curing the polymerizable composition, the analyte of interest can be extracted to provide molecular imprints for the analyte of interest in the contact lens.

A contact lens, which is capable of binding the analyte of interest, can be made from a composition containing a component or part thereof (e.g., receptors) which is capable of binding the analyte of interest.

The invention, in one aspect, provides a method for determining the fertility status of a current ovulation cycle of a female human, comprising the steps of: (a) monitoring variation in tear concentration of at least one hormone of relevance to female fertility; and (b) evaluating the correspondence of the variation in tear concentration of said hormone to onset of the transition phase, fertile phase, ovulation, or infertile phase of a menstrual cycle in said female human, wherein the step of monitoring is performed by periodically collecting a tear fluid from the female human and then determining the tear concentration of said hormone.

Exemplary hormones of relevance to female fertility include, without limitation, estrogen (including, e.g., estradiol), luteinizing hormone (LH), progesterone and follical stimulating hormone (FSH).

The first collection of tear fluid in a current cycle is made at the cessation of menses, preferably at least 3 days, more preferably at 5 days calculated from the onset of menstruation. The periodicity of tear collection can be once every two days, preferably once a day. However, the accuracy of the prediction of the onset of the fertile period is somewhat dependent upon the periodicity of the tear collection. It is desirable in the practice of the method of the invention that periodical collections of tear fluids occur at approximately the same each day.

Where a capillary glass tube or a hydrogel strip is used to collect tears, the periodical collections of tear fluids preferably occur each day upon waking or at approximately a fixed time in the morning.

Where a contact lens is used to collect tears, contact lenses are preferably worn by a user for a period of at least 15 minutes, preferably at least 30 minutes, even more preferably at least one hour, for the purpose of reaching the distribution equilibrium between the tear and the lens. More preferably, the periodical collections of tear fluids occur at the end of each day, after one day's wear.

Where variation of the tear concentration of estrogen (e.g., estradiol) is monitored, a significant increase in tear concentration or a determined tear concentration being higher than a reference value (i.e., threshold value), following the cessation of menses, is indicative of the onset of the fertile period.

Where variation of the tear concentration of luteinizing hormone is monitored, detection of an LH surge or a determined tear concentration being higher than a reference value (i.e., threshold value), indicates to the user with a very high degree of certainty that the user will no longer be fertile four days hence (3 days after ovulation). Also, the day of the cycle on which ovulation has occurred can be noted for future reference.

Where variation of the tear concentration of progesterone is monitored, the end of the fertile period (though not so accurately the day of ovulation) can be predicted by detecting a significant increase in progesterone concentration or by detecting a concentration being higher than a reference value (i.e., threshold value) following the cessation of menses. Progesterone has a relatively low level in tears until the start of the luteal phase, at which point its level rises fairly sharply. Therefore, once a significant increase in progesterone tear concentration is recorded, it can be indicated to the user that the luteal phase of the cycle-i.e., the terminal infertile period--has commenced. Once a significant increase in progesterone tear concentration is recorded, a user can be advised that she is infertile for the remainder of that cycle.

If desired, the detection of either LH or progesterone can be used as a trigger to indicate that the subject is no longer fertile until the end of the cycle, with one hormone acting as a "back up" to the other. However, it is preferred that the detection of LH be used as a primary indicator of whether ovulation has or is about to occur, since the detection of LH lends itself to more accurate determination of the exact ovulation day than the use of progesterone.

If desired, the detection of at least two of estrogen, LH and progesterone can be used to determine the status of a menstrual cycle of female human.

In a particularly preferred embodiment, both estrogen (e.g., estradiol) and progesterone are determined and the tear concentration ratio of estrogen (e.g., estradiol) to progesterone are used to determine the fertility status of a current ovulation cycle of a female human. Once the tear concentration ratio of estradiol to progesterone increases significantly (i.e., a significant increase) or is higher than a reference value (i.e., a threshold value), following the cessation of menses, it can be indicated to the user the onset of the fertile period. It is believed that by periodically monitoring the tear concentration ratio of estradiol to progesterone, a more pronounced peak in the tear concentration ratio of estradiol to progesterone can be observed. For a method based on the periodically monitoring of the tear estradiol concentration alone, two peaks, which are not well separated, can be observed. The accuracy of the fertility prediction can be compromised.

The base level of an hormone in tear immediately following menses can be obtained by determining the tear concentration of that hormone on any day in the period from day 1 up to and including day 6 calculated from the onset of menses, preferably by averaging at least two tear concentrations of that hormone determined on two different days in the period from day 1 up to and including day 6 calculated from the onset of menses. Alternatively, the base level of an hormone in tear immediately following menses can be established by tests conducted in the period, from day 1 up to and including day 6 calculated from the onset of menses, of one or more previous cycles (up to 10 cycles), preferably consecutive cycles immediately preceding the current cycle.

For practical purposes, the threshold can be defined as the hormone concentration which is exceeded more frequently during the transition phase than during the infertile phase. For example, it may be exceeded on not more than 30% of the days in the infertile phase, but exceeded on not fewer than 60% of the days in the transition phase. More preferably the threshold is the hormone concentration which is exceeded on not more than 20% of the days in the infertile phase, but which is exceeded on not fewer than 80% of the days in the transition phase.

The threshold value of tear hormone concentration should be determined from measurements of estrogen or LH concentration during the transition and pre-fertile phases of one or more previous cycles. While the threshold for the individual subject is being established, regular (preferably daily) measurements of tear hormone concentration should be taken during these phases over at least one cycle and more preferably over at least two cycles, and ideally over at least three cycles. When more than one establishing cycle is used, these are preferably consecutive.

After an appropriate hormone threshold has been established, regular hormone testing can be discontinued during the early part of the infertile phase of the current cycle. Instead, testing can be commenced at a set time after the onset of menses.

The invention, in another aspect, provides a method for determining the fertility status of a current ovulation cycle of a female human, comprising a series of steps performed at least once per day for at least several days preceding and following ovulation, said steps comprising: (a) collecting a tear fluid from the female human; (b) determining variation in tear concentration of at least one hormone of relevance to female fertility to establish variation in tear concentration of said hormone; and (c) evaluating the correspondence of the variation in tear concentration of said hormone to onset of the fertile phase, ovulation, or infertile phase of a menstrual cycle in said female human.

Such method has the advantage in that it may require less testing within a given month, and hence reduced expense and inconvenience to the user, without any prejudice to the reliability.

In a preferred embodiment, the method further comprises testing of the tear concentration of said hormone in relation to the status of the ovulation cycle during the pre-ovulation phase, wherein testing for said analyte is conducted at least once in the period from day 1 up to and including day 7 calculated from the onset of menses (day 1 being the day on which menstruation is first observed), to establish a base concentration value or signal for said hormone in the current cycle.

Preferably, the base concentration value is established from test(s) conducted in the period from day 1 up to and including day 7, more preferably from test(s) conducted on day 5 and/or day 6, and most preferably from a single test conducted on day 6.

It is generally envisaged that there can be a gap of at least one day, and more usually several days, between establishment of the base concentration value and the commencement of daily testing, during which gap no testing need be conducted. Thus, in one option, the user performs a single test during the infertile phase following the onset of menses, e.g., on day 6, and several days later commences a relatively brief schedule of daily testing, which is terminated after sufficient information has been derived to identify the fertile phase, preferably including an indication of the end of the fertile phase in that cycle. Typically this termination of testing will be on the day of LH surge and/or a significant increase in progesterone tear concentration, or within a few days thereafter, so that the remainder of the cycle is test-free.

The present invention also provide a family planning (birth control or intercourse timing) method based on the aforementioned methods for determining the fertility status of a current ovulation cycle of a female human. It is generally accepted that the maximum survival function of spermatozoa capable of fertilizing an ovum is approximately three days following coitus. Although theoretically any coitus prior to ovulation entails a certain risk of pregnancy, as a practical matter, abstinence from unprotected sexual intercourse for at least 3 days (preferably up to 5 days) prior to ovulation is generally considered sufficient to avoid pregnancy. It is generally recognized that a human ovum is (in vivo) fertilizable for about 12 hours and certainly for no more than 1 day following ovulation. The human fertile period, then, is made up of no more than 4 to 6 days out of the entire menstrual cycle. If it were possible to accurately predict this fertile period, in order to avoid pregnancy it would only be necessary to abstain from unprotected intercourse or use alternate birth control methods during that 4-6 day "fertile period" rather than for the entire menstrual cycle.

The present invention, in still another aspect, provides a birth control (or intercourse timing) method, comprising the steps of: (a) monitoring variation in tear concentration of at least one hormone of relevance to female fertility; (b) evaluating the correspondence of the variation in tear concentration of said hormone to onset of the fertile phase, ovulation, and/or terminal infertile period of a menstrual cycle in said female human; and (c) causing said female human to avoid exposure to fertilization beginning at least at the onset of the fertile phase and ending day "+2" relative to the day of actual ovulation, wherein the step of monitoring is performed by periodically collecting a tear fluid from the female human and then determining the tear concentration of said hormone.

The invention, in a further aspect, provides a birth control (or intercourse timing) method, comprising a series of steps performed at least once per day for at least several days preceding and following ovulation, said steps comprising: (a) collecting a tear fluid from the female human; (b) determining variation in tear concentration of at least one hormone of relevance to female fertility to establish variation in tear concentration of said hormone; (c) evaluating the correspondence of the variation in tear concentration of said hormone to onset of the fertile phase, ovulation, and/or terminal infertile period of a menstrual cycle in said female human; and (c) causing said female human to avoid exposure to fertilization beginning at least at the onset of the fertile phase and ending day "+2" relative to the day of actual ovulation.

By using the birth control method of the present invention, contraceptive methods, such as abstinence; contraceptive materials, such as spermicidal foams; or contraceptive devices, such as condoms or diaphragms, need be used for only a portion of the overall menstrual cycle.

In accordance with the present invention, the tear concentration of a hormone may be measured in absolute terms, or in relative terms e.g. as a ratio relative to the concentration of a reference analyte or hormone present in the same sample of tear fluid, or in cumulative terms, e.g., the quantity of a hormone accumulated in a hormone collecting device over a period of time.

Generally, it will be sufficient to assay a hormone in a manner which yields a signal, convertible to numerical data, related to the actual concentration, so that such data can be compared with similar data obtained at a different stage in the cycle to determine whether or not a significant change in actual concentration has occurred. Accordingly, where the specification and claims below refer to the "concentration" of a hormone, this expression should be interpreted broadly.

It is well known to a skilled artisan that assay of an analyte of interest can be carried out with the help of a testing agent composition which specifically reacts or interacts with the analyte of interest, leading to formation of a detectable signal. A detectable signal, for example, can be radio signals (i.e., radioactive isotopes), electrical signals, or optical signals. Exemplary electrical signals are electrical potentials and currents. Optical signals refers to changes in the optical properties, including, but not limited to, a color formation, a change in color, fluorescence, luminescence, chemiluminescence, changes in fluorescence or luminescence intensity, changes in fluorescence or luminescence lifetimes, fluorescent anisotropy or polarization, a spectral shift of the emission spectrum, time-resolved anisotropy decay, and the like.

Any know suitable assays can be used in the present invention. Exemplary assays include, without limitation, radioimmunoassay (RIA), enzyme immunoassay (EIA), immunofluorescence assay (IFA), enzyme-linked immunosorbent assay (ELISA), assays based on Trinder reaction, electrochemical assay, and the like.

The invention, in another further aspect, provides a method for monitoring the status of women's health, comprising the steps of: (a) collecting a tear fluid from the female human; (b) determining the tear concentration of at least one hormone of relevance to female fertility, sexual differentiation or sexual dysfunction in a female human, wherein the tear concentration is diagnostic of the status of women's health.

In alternative preferred embodiments, the tear concentration of human chorionic gonadotropin (hCG) is monitored for pregnancy tests, the tear concentration of follicle stimulating hormone (FSH) is monitored for menopausal diagnosis, the tear concentration of one or more estrogens (e.g., estradiol and/or progesterone) is monitored to determine the amount of hormones required in hormonal replacement therapy, the tear concentration of testosterone, sex hormone binding globulin, progesterone, LH, FSH and/or prolactin is determined to monitor polycystic ovarian disease, and the tear concentration of testosterone is determined to diagnose female sexual dysfunction (FSD).

The invention further provides kits for determining the fertility status of a current ovulation cycle of a female human, for birth control, and for monitoring the status of women's health. A kit of the invention comprises a plurality of tear-collecting devices, a testing reagent composition which specifically reacts or interacts with at least one hormone of relevance to female fertility, sexual differentiation or sexual dysfunction in a female human to form a detectable signal which changes in a concentration-dependent manner, and optionally instruction for an user.

Similarly, the above described methods and kits can be used to predict the fertile period of a female animal to ensure that fertilization occurs and the offsprings are produced. This determination is useful to owners of pets, such as cats and dogs, as well as to breeders of livestock and particularly to breeders of thoroughbred race horses or cattles.

In a still further aspect, the present invention provides a method for determining the fertility status of a current ovulation cycle of a female non-human mammal, comprising the steps of: (a) monitoring variation in tear concentration of at least one hormone of relevance to female fertility; and (b) evaluating the correspondence of the variation in tear concentration of said hormone to onset of the transition phase, fertile phase, ovulation, or infertile phase of a menstrual cycle in said female nonhuman mammal, wherein the step of monitoring is performed by periodically collecting a tear fluid from the female nonhuman mammal and then determining the tear concentration of said hormone.

Non Human mammals include, without limitation, domestic cattle, horses, pig, goats, sheep, lamas, cats, dogs, rabbits, hamsters, mice and rats.

The previous disclosure will enable one having ordinary skill in the art to practice the invention. In order to better enable the reader to understand specific embodiments and the advantages thereof, reference to the following examples is suggested.

EXAMPLE 1

A DAILIES® contact lens, made of a modified polyvinylalcohol (Nelfilcon A), was placed in one of the wells of a 24-well plate. Each well contains 1 ml of a progesterone solution (70 nmol/L of progesterone which is within the range of a physiological concentration). The lens was soaked in the progesterone for 12 hours and then washed thoroughly and extracted via vacuum for any progesterone. A commercially available immunoassay kit (Bioclone) was used to determine how much progesterone had been absorbed into the lens. The results indicated that the contact lens had taken up approximately 3% of total amount of progesterone in the soaking solution.

EXAMPLE 2

Polyacrylic acid (PAA) solution: A PM solution (0.001 M, pH 2.5) is prepared from a polyacrylic acid having a molecular weight of about 90,000, from Polyscience, Inc. The PM concentration is calculated based on the repeating unit in PM. Poly(allylamine hydrochloride) (PAH) solution: A PAH (0.001M, pH ~4.3) is prepared from a PAH having a molecular weight of about 60,000, from Aldrich. The PAH concentration is calculated based on the repeating unit in PAH. Coating A (PAA/PAH/PAA/PAH/PAA/PAH/PAA/PAH/PAA/PAH): An LbL coating having 4 bilayers of PAA/PAH is formed on a DAILIES® contact lens, made of a modified polyvinylalcohol material, Nelfilcon A, (CIBA Vision). The contact lens is dipped with the help of a Zeiss coater in a PM solution (0.001 M, pH 2.5) for 30 minutes to form the innermost layer of the coating on the lens and then rinsed with water by dipping with the help of a Zeiss coater in water for I minute. The lens with the innermost layer of PM is then dipped with the help of a Zeiss coater in a PAH solution (0.001 M, pH ~4.3) for 5 minutes, rinsed with water by dipping with the help of a Zeiss coater in water, dipped with the help of a Zeiss coater in the PM solution (0.001 M, pH 2.5) for 5 minutes, and then rinsed by dipping with the help of a Zeiss coater in water. The steps of alternatively dipping with the help of a Zeiss coater in the PM solution for 5 minutes and in PAH solution for 5 minutes are repeated for a number of time to build up 4 bilayers (i.e., PA/PAH/PM/PAH/PAA/PAH/PA/PAH) with a capping layer of PAH on the lens. The capping layer of coating A is a PAH layer. Coating B (PAA/PAH/PAA/PAH/PAA/PAH/PAA/PAH/PAA): An LbL coating having 4 bilayers of PA/PAH and a capping layer of PM is formed on a DAILIES® contact lens, made of a modified polyvinylalcohol material, Nelfilcon A, (CIBA Vision). The contact lens is dipped with the help of a Zeiss coater in a PM solution (0.001M, pH 2.5) for 30 minutes to form the innermost layer of the coating on the lens and then rinsed with water by dipping with the help of a Zeiss coater in water for 1 minute. The lens with the innermost layer of PM is then dipped with the help of a Zeiss coater in a PAH solution (0.001 M, pH ~4.3) for 5 minutes, rinsed with water by dipping with the help of a Zeiss coater in water, dipped with the help of a Zeiss coater in the PM solution (0.001 M, pH 2.5) for 5 minutes, and then rinsed by dipping with the help of a Zeiss coater in water. The steps of dipping with the help of a Zeiss coater in the PAH solution for 5 minutes followed by dipping with the help of a Zeiss coater in the PM solution for 5 minutes are repeated for 3 additional times to build up 4.5 bilayers (i.e., PAA/PAH/PA/PAH/PAA/PAH/PAA/PAH/PM) on the lens. The capping layer of coating B is a PM layer.

Contact lenses without LbL coating, with coating A and with coating B are placed in wells of a 24-well plate (one lens in one well). Each well contains 1 ml of an enzyme-labeled LH solution. Each contact lens is soaked in an enzyme-labeled LH solution overnight. The tested concentrations of enzyme-labeled luteinzing hormone is ranged from 0.1 µg/mL to 0.5 mg/ml. After soaking, the lenses are washed thoroughly and assayed for the presence of enzyme-labeled LH. Results show that the lenses with coating B (with a capping layer of PM ) absorb LH significantly higher than the lenses without coating or the lenses with coating A (with a capping layer of PAH).

EXAMPLE 3

A DAILIES® contact lens, made of a modified polyvinylalcohol material, Nelfilcon A, (CIBA Vision) is coated to form an LBL coating (PAA/PAH/PAA/PAH/PAA/PAH/PAA/PAH/PAA) as described in Example 2 (Coating B). The LbL coating provided a surface with free COOH groups to which the amine groups of an LH monoclonal antibody are covalently attached by using EDC/s-NHS coupling as follows.

LH antibody-horseradish peroxidase (HRP) conjugate is prepared by using EZ-Link Maleimide Activated HRP kit from Pierce according to the procedure recommended by the supplier. The obtained LH antibody—HRP conjugate is used to prepare a conjugate solution (0.16 mg/ml in water).

An EDC/s-NHS solution is prepared by dissolving 100 mg of EDC (1-Ethyl-3-(3-dimethylaminopropyl)) and 220 mg of s-NHS (N-Hydroxysulfosuccinimide) in 10 ml water. 5 ml of the above-prepared EDC/s-NHS solution is mixed with 5 ml of the above-prepared LH antibody-HRP conjugate solution and the pH of the solution is adjusted to about 9.0 to obtain a crosslinking solution.

Each contact lens with coating B is placed in a well of a 24-well plate. Each well contains 1 ml of the crosslinking solution. Each lens is soaked in the covalent attachment solution at 4° C. overnight. After overnight soaking, each lens is rinsed 4 times with PBS (1 hour per rinse). After final rinse, each lens is transferred to one of the wells of a clean 24-well plate (1 lens per well) and soaked in OPD substrate solution (o-Phenylenediamine). At the reaction endpoint, 100 µL of aliquots from each well are placed in a 96-well plate and the absorption at 450 nm is determined to calculate the amount of LH antibody-HRP conjugate covalently attached to the lens. It is found that in average 80 ng of LH antibody-HRP conjugate is covalently attached to each DAILIES lens with coating B. Such amount of LH antibody-HRP conjugate is shown to be sufficient to attract LH from the tear film enabling direct measurement of the presence of LH from the lens.

EXAMPLE 4

Serum and reflex tear samples were collected from five different female subjects on day 5 and day 22 of their cycle, since Progesterone has been found to surge approximately 7 days post ovulation, that is, around day 22 of a menstrual cycle (Tietz Fundamentals of Clinical Chemistry, fifth edition). Assayed for progesterone were carried out using progesterone EIA (Assay Designs, Ann Arbor, Mich., USA). The results were then translated from absorbance units to nmol/L amounts using a 4-parameter logistic plot, and are expressed below. The static point data showed that there is a statistically significant difference in progesterone concentration between Day 5 and Day 22 in both serum and tears, showing that a surge can be detected when expected in both these fluids. However, it has also been found that the total concentrations in serum are significantly different to tears (i.e., about 2-fold less in tears).

EXAMPLE 5

18 female subjects were recruited for one whole menstrual cycle. Each subject was given a Clearplan Fertility monitor which determines the surge in both estradiol-17-glucuronide and LH. In determining when these hormones surged it was possible to decide when sample collection was necessary. Typically samples were taken on about 8 key days in the cycle. These days corresponded with a baseline time, such as day 5, 3 days when the estradiol and LH were surging and 4 consecutive days which started 7 days post the LH surge.

Figure 1B:
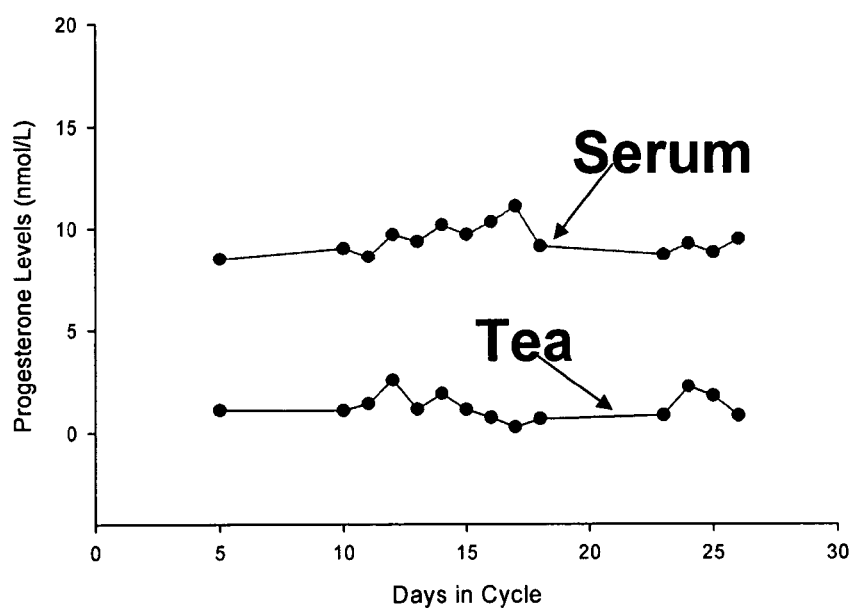
FIG. 1B shows correlation of progesterone in tears and serum of patient B.

The serum and tear samples from each of these days were assayed for progesterone using progesterone EIA (Assay Designs, Ann Arbor, Mich., USA), ensuring all samples were diluted 1/10 in the assay buffer provided in the kit prior to the assay. The results were then calculated and plotted for each individual. It has been found that there exists correlation of progesterone in tears and serum for a given individual. For example, FIGS. 1A and 1B show some examples. It can be noticed clearly that in FIG. 1A the concentration of progesterone in serum is very closely mimicked by tears (for patient A). Although tear concentrations were approximately half those of serum, it was evident that a tight correlation exits. Such correlation of progesterone in tears and serum was also observed in a different patient (patient B) as shown in FIG. 1B. The subject in this graph showed no LH surge (monitored by using a "ClearPlan Easy" fertility monitor (Unipath Diagnostics Company) and thus showed no progesterone surge in serum. This again was reflected in the tears. The conclusion for this data is that a surge or lack of surge in serum is always reflected in the tear film concentrations of progesterone.

The ratio between surge and non-surge states was calculated for serum and tears for the patients. Table 1 shoes ratio between surge and non-surge of progesterone for both serum and tears. As can be seen in Table 1, when a surge is detected in serum a surge is always detected in tears. It has been found that in the majority of cases the ratio difference in surge states for tears was always much greater than that for serum. This appears to be due to a threshold effect in the tear film. At non-surge states of progesterone there is much less present in tears than serum, however, at surge times the difference between serum and tear concentrations is much less. This may indicate that progesterone starts to flood into the tears at a certain physiological threshold, thus giving a greater difference between surge and non-surge states.

TABLE 1

| Subject ID | Tear Surge/Non-Surge Ratio | Serum Surge/Non-Surge Ratio |
|---|---|---|
| TH02 | 1.92 | 1.47 |
| TH03 | 4.84 | 3.04 |
| TH04 | 7.35 | 2.57 |
| TH07 | 5.56 | 3.02 |
| TH09 | 2.04 | 1.64 |
| TH10 | 10.1 | 2.3 |
| TH11 | 4.10 | 2.90 |
| TH13 | 4.0 | 2.4 |
| TH14 | 4.05 | 3.49 |
| TH15 | 15.30 | 2.98 |
| TH19 | 4.81 | 3.05 |
| TH20 | 7.3 | 6.4 |
| TH21 | 8.58 | 2.48 |
| TH23 | 13.44 | 3.46 |
| TH24 | 3.56 | 2.34 |
| TH25 | 4.43 | 1.94 |

EXAMPLE 6

Serum and reflex tear samples were collected from four different female subjects on day 5 and day 14 of their cycle, since estradiol has been found to surge approximately 2-3 days prior to the LH surge, that is, around day 12-14 of a menstrual cycle (Tietz Fundamentals of Clinical Chemistry, fifth edition). After these samples were taken, they were assayed for 17β estradiol using a 17β estradiol EIA (Diametra, Italy). The results were then translated from absorbance units to pg/mL amount, and are expressed below. The static point data showed that there is a statistically significant difference in 17β estradiol concentration between Day 5 and Day 14 in both serum and tears, showing that a surge can be detected when expected in both these fluids. Also, in comparing the data from the two different fluids, it is also evident that the total concentrations in serum are not significantly different to tears.

EXAMPLE 7

Reflex tears were collected from 3 male and 3 female subjects. The male tears were pooled and the female tears were pooled separately and run in a testosterone EIA (Bioclone, Sydney, Australia). In comparing female to male tears, there was significantly more testosterone in the male tears.

EXAMPLE 8

A panel of 25 potential subjects were enrolled in the first phase of the study. To qualify for the study, the subject had to be a non-pregnant female between the ages of 18 and 35, who were not on pharmacological contraception, antibiotic, or hormone therapy. Any other medication the subject was taken had to be declared before enrollment. During this time each subject was provided with a "ClearPlan Easy" fertility monitor (Unipath Diagnostics Company). They tested their own first morning urine each morning for one month with the monitor, while noting their key days of fertility. At the end of the month, each data sheet was collected and analysed for strong fertility and reliable cycle. The most suitable 18 subjects were recruited for the next phase of the study.

During the next phase of the study, each subject continued to check their first morning urine each day and, by analyzing their data sheet, were told when to come in to provide tear and serum samples. The exact days and duration of this phase was dependent on each subject's individual cycle. This phase required no less than 8 and no more than 16 sample days.

The first sample day for each subject was between day 1 and day 5 of their cycle. On this and subsequent sample days tears, blood and urine samples were collected from each subject. Each subject collected their own first morning urine upon awakening, and brought it to the clinic in a sterile container within 4 hours. Blood samples were collected by venupuncture and reflex tears were self collected by capillary tubes.

The serum and tear samples were sent to the CIBA Vision's research laboratory where they were assayed for progesterone, LH and estradiol.

Tears were only assayed for progesterone and estradiol, not for LH. LH was assayed in the blood to confirm that all samples were taken at the correct times. A representative graph below shows the LH peak in the serum, which matched perfectly with the fertile days reflected in the urine.

As shown below, there was 6-7 days between the LH surge and the progesterone surge, indicating the potential of steroid hormone measurement to predict the fertile period.

| Subject ID | Serum LH surge days | Tear progesterone surge days |
|---|---|---|
| TH24 | 16 | 22 |
| TH03 | 15 | 21, 22, 23, 24 |
| TH19 | 19 | 26 |
| TH25 | 20, 21 | 27, 28 |

What is claimed is:

1. A method for determining a fertility status of a current ovulation cycle of a female human, comprising the steps of:
    (a) monitoring variation in tear concentration of at least one hormone of relevance to female fertility; and
    (b) evaluating a correspondence of the variation in tear concentration of said hormone to onset of a transition phase, fertile phase, ovulation, or infertile phase of a menstrual cycle in said female human, wherein the step of monitoring is performed by periodically collecting a tear fluid from the female human by use of a hydrogel soft contact lens and then determining the tear concentration of said hormone in the tear fluid;

wherein said hydrogel soft contact lens is capable of binding said hormone;

wherein the hydrogel soft contact lens includes: (1) surface charges present in a density sufficient to impart to the contact lens an increased adsorption of said hormone;

or (2) molecular imprints for said hormone.

2. The method of claim 1, wherein the tear fluid is collected daily by (1) placing the contact lens in the eye of the female human; (2) minimizing or eliminating biological concentration variability of said hormone in the tear fluid by wearing the contact lens on the eye for at least 30 minutes; and (3) by removing the contact lens from the eye.

3. The method of claim 2, wherein the first collecting of tear fluid in the current ovulation cycle is made at least at 3 days following an onset of menses.

4. The method of claim 2, wherein said hormone is estrogen, and wherein a significant increase in estrogen tear concentration or a determined estrogen tear concentration being higher than a threshold value, following a cessation of menses, is indicative of a onset of a fertile period.

5. The method of claim 2, wherein said hormone is LH, wherein detection of a LH surge or a determined LH tear concentration being higher than a threshold value, indicates that the female human will no longer be fertile four days hence 3 days after ovulation.

6. The method of claim 2, wherein said hormone is progesterone, wherein the end of the fertile period can be predicted by detecting a significant increase in progesterone tear concentration or by detecting a progesterone tear concentration being higher than a threshold value following the cessation of menses.

7. The method of claim 2, wherein at least two of estrogen, LH and progesterone are monitored to determine the status of a menstrual cycle of the female human.

8. The method of claim 2, wherein estrogen and progesterone are monitored to determine the fertility status of a menstrual cycle of the female human.

9. The method of claim 8, wherein the estrogen is estradiol, wherein a significant increase in the tear concentration ratio of estradiol to progesterone or a determined value of the tear concentration ratio of estradiol to progesterone being higher than a threshold value, following a cessation of menses, is indicative of a onset of a fertile period.

10. A method for determining the fertility status of a current ovulation cycle of a female human, comprising a series of steps performed at least once per day for at least several days preceding and following ovulation, said steps comprising: (a) collecting a tear fluid from the female human by the use of a hydrogel soft contact lens; (b) determining variation in tear concentration of at least one hormone of relevance to female fertility to establish variation in tear concentration of said hormone; and (c) evaluating the correspondence of the variation in tear concentration of said hormone to onset of the fertile phase, ovulation, or infertile phase of a menstrual cycle in said female human; wherein said hydrogel soft contact lens is a contact lens capable of binding said hormone; wherein the hydrogel soft contact lens includes: (1) surface charges present in a density sufficient to impart to the contact lens an increased adsorption of said hormone; or (2) molecular imprints for said hormone.

11. The method of claim 10, wherein the tear fluid is collected daily by (1) placing the contact lens in the eye of the female human; (2) minimizing or eliminating biological concentration variability of said hormone in the tear fluid by wearing the contact lens on the eye for at least 30 minutes; and (3) by removing the contact lens from the eye.

12. The method of claim 11, wherein the tear fluid is collected daily after wearing for more than 6 hour.

13. The method of claim 11, wherein said hormone is estrogen, and wherein a significant increase in estrogen tear concentration or a determined estrogen tear concentration being higher than a threshold value, following the cessation of menses, is indicative of the onset of the fertile period.

14. The method of claim 11, wherein said hormone is LH, wherein detection of a LH surge or a determined LH tear concentration being higher than a threshold value, indicates that the female human will no longer be fertile four days hence 3 days after ovulation.

15. The method of claim 11, wherein said hormone is progesterone, wherein a end of a fertile period can be predicted by detecting a significant increase in progesterone tear concentration or by detecting a progesterone tear concentration being higher than a threshold value following a cessation of menses.

16. The method of claim 11, wherein at least two of estrogen, LH and progesterone are monitored to determine the status of a menstrual cycle of the female human.

17. The method of claim 11, wherein estrogen and progesterone are monitored to determine the fertility status of a menstrual cycle of the female human.

18. The method of claim 17, wherein the estrogen is estradiol, wherein a significant increase in the tear concentration ratio of estradiol to progesterone or a determined value of the tear concentration ratio of estradiol to progesterone being higher than a threshold value, following a cessation of menses, is indicative of a onset of a fertile period.

19. The method of claim 11, further comprising conducting at least one test for the tear concentration of said hormone in a period from day 1 up to and including day 7 calculated from a onset of menses, to establish a base concentration value or signal for said hormone in a current cycle.

20. The method of claim 19, wherein the base concentration value is established from test(s) conducted on day 5 and/or day 6 from a onset of menses.

* * * * *